United States Patent [19]
Nelson

[11] Patent Number: 5,681,271
[45] Date of Patent: Oct. 28, 1997

[54] ANKLE BRACE WITH RELIEF

[76] Inventor: Ronald E. Nelson, 1120 Second St., Box 441, Chetek, Wis. 54728

[21] Appl. No.: 533,206

[22] Filed: Sep. 25, 1995

[51] Int. Cl.⁶ .................................................. A61F 3/00
[52] U.S. Cl. ........................ 602/27; 602/65; 128/882
[58] Field of Search .......................... 602/5, 27, 65, 602/23, 60, 61, 62, 63, 66; 128/882

[56] References Cited

U.S. PATENT DOCUMENTS

| | | | |
|---|---|---|---|
| 851,950 | 4/1907 | Le Mat | 602/27 |
| 938,440 | 10/1909 | Sescila | 602/27 |
| 1,374,669 | 4/1921 | McClellan | 602/27 |
| 4,084,586 | 4/1978 | Hettick | 602/27 |
| 4,187,844 | 2/1980 | Caprio, Jr. | 602/27 |
| 4,280,488 | 7/1981 | Polsky et al. | 602/27 |
| 4,727,863 | 3/1988 | Nelson | 602/27 |
| 4,878,504 | 11/1989 | Nelson | 602/27 |

Primary Examiner—Richard J. Apley
Assistant Examiner—Kim M. Lee
Attorney, Agent, or Firm—Burd, Bartz, Gutenkauf

[57] ABSTRACT

An ankle brace includes an outer layer of flexible, inelastic material and an inner layer of elastic material. The outer layer has a plurality of relief openings that are strategically located according to locations of flexure and extension of the foot and ankle, thereby to allow additional extension of the brace to accommodate extension of that portion of the brace, and to alleviate bunching of the material when the portion of the brace is placed in flexure. Relief openings are located on the front superior foot surface on either side of the base and also near the sole of the foot in association with the front edge of the base. A support strap system is provided to protect the foot upon inversion and eversion.

10 Claims, 2 Drawing Sheets

ANKLE BRACE WITH RELIEF

BACKGROUND OF THE INVENTION

The ankle brace finds widespread use for the protection of the ankle against moderate to severe injury, and for protection against aggravation to pre-existent injury. The ankle joint, while very stable and resistant to injury, is one of the most used and abused joints, particularly upon participation in certain rugged activity, such as the sports of basketball and football.

The ankle brace has found acceptance in favor of other ankle support mechanisms, such as the elastic wrap or tape. Most ankle braces include a base that is configured to be wrapped around the foot and ankle in a substantially conforming relationship, and secured by lacing at closeable forward edges that come together over the front superior foot surface. The base fits closely and comfortably when the foot is in a neutral or un-flexed posture. Upon flexure of the foot or inward bending, or upon extension of the foot or outward bending, the brace no longer conforms as closely to the foot. The inelasticity of the flexible shell of the base compromises the integrity of the fit upon flexion and extension of the ankle. This is particularly true at the front superior foot surface area in the vicinity of the transition between the ankle and foot, and on the side of the base in the vicinity of the sole of the foot near the ball of the foot.

Upon flexure of the foot, the base of the ankle brace tends to bunch at the front superior foot surface area along the lacing. At the same time, the forward edge of the base near the ball of the foot is put in tension which can unduly restrict further movement of the foot relative to the lower leg in flexure. In extension, the opposite occurs. The area of the base along the front superior foot surface and parallel to the lace openings, is placed in tension while there is some amount of bunching along the front edge near the sole in the vicinity of the ball of the foot. In the use of flexible but inelastic base material, such reaction is difficult to avoid. A completely elastic base, on the other hand, compromises support to the ankle.

SUMMARY OF THE INVENTION

The invention pertains to an ankle brace that more closely conforms to the foot and ankle of a wearer when the ankle is in a position of flexure or extension. The brace includes a base of flexible material configured to be wrapped in close conformance around the foot and ankle of the wearer. Forward edges close around the front superior foot surface and come toward each other to be secured by appropriate means such as a lace. The base has a front edge that wraps around the front portion of the foot. The base has two substantially coextensive layers. One layer is a flexible inelastic layer formed of a material such as vinyl. The other is a flexible and elastic layer. The two layers are fixed by suitable means such as sewing. The outer layer or shell of inelastic material has relief openings cut out of it. They are located on either or both sides of the base at locations of bunching or excess tension upon flexure or extension of the foot and ankle. The elastic layer spans these openings. One such opening is comprised as an elongate, arcuate-shaped or notch-shaped opening disposed on the base in the vicinity of the front superior foot surface at the juncture of the foot and ankle. This opening has a longitudinal axis that is generally parallel to the curvature of the front superior foot surface at the juncture of the ankle and foot. Such an opening is located on either side of the base. Another such opening is located at the front edge of the base that wraps around the foot. This opening is comprised as a V-Shaped notch or a triangular-shaped opening with one edge coextensive with the front edge of the base.

In a preferred embodiment, support straps are sewn to the interior surface of the base. One strap extends from below the foot in the region of the heel to the forward edge along the lace eyelet column. This strap is fixed intermediately and serves to protect the interior talofibular ligament. Another strap, also located on the anterior distal side of the base, extends from the front edge of the base up along the base a short distance generally parallel to the row of lace eyelets. This strap protects the foot upon inversion and eversion.

IN THE DRAWINGS

FIG. 3 is an enlarged view of a portion of the ankle brace of FIG. 1;

DESCRIPTION OF A PREFERRED EMBODIMENT

Figure 1:
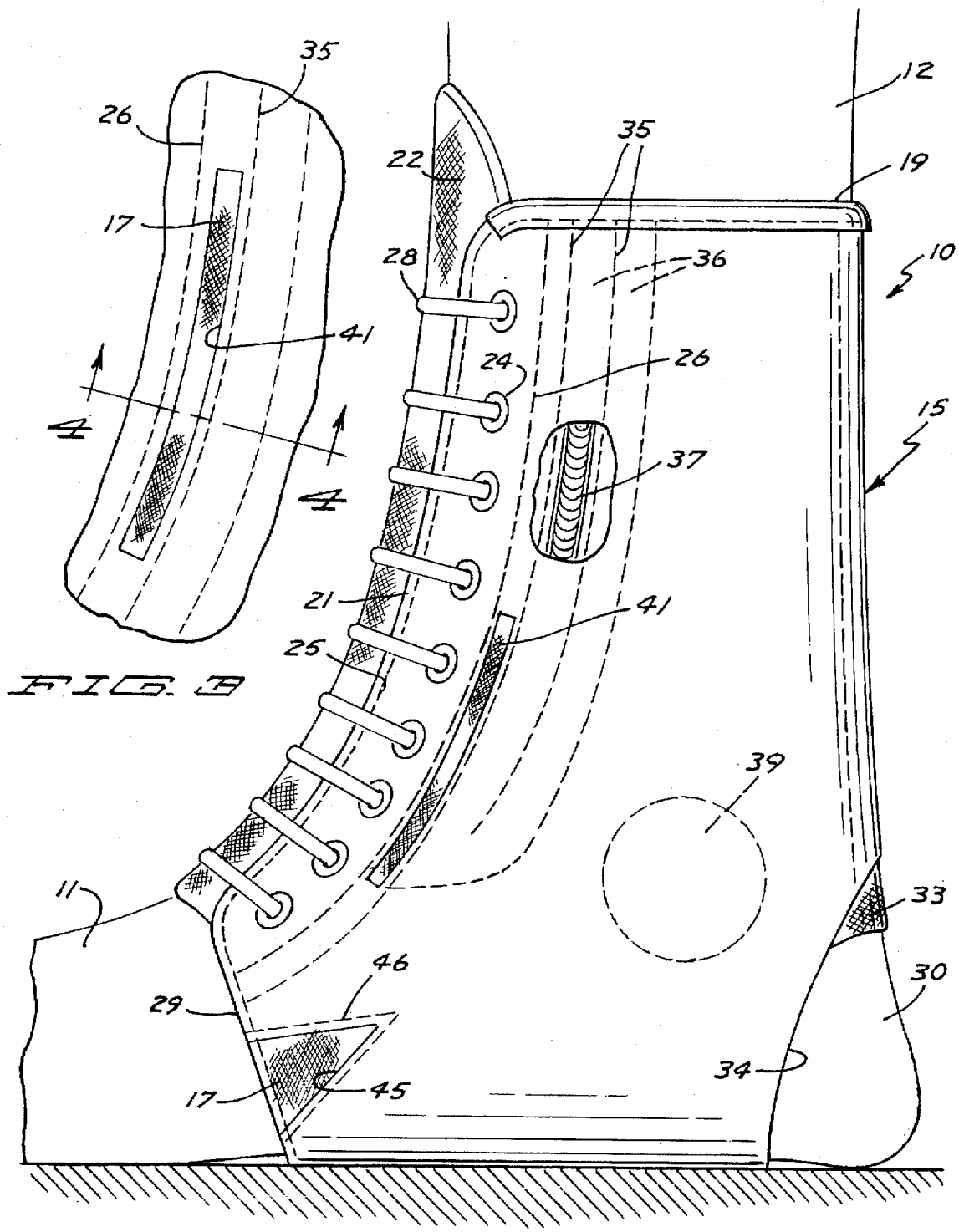
FIG. 1 is a side elevational view of an ankle brace according to the invention installed on the right foot of a wearer.

Referring to the drawings, there is shown in FIG. 1 an ankle brace according to the invention indicated generally at 10, installed on a right foot 11 and ankle 12. The brace 10 comfortably supports the foot 11 and ankle 12 in conjunction with the lower leg, and provides protection against injury and aggravation to pre-existent injury.

Figure 2:
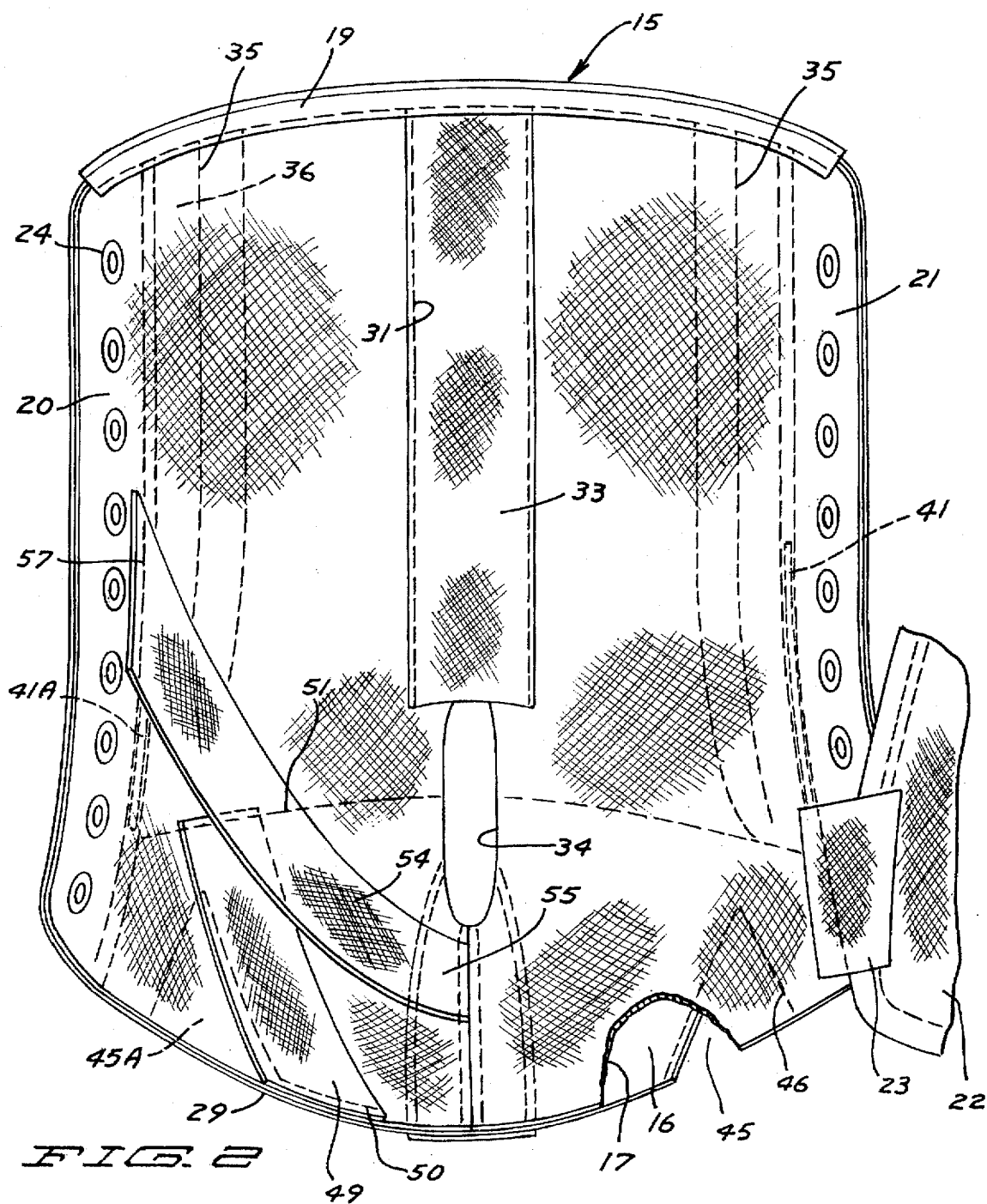
FIG. 2 is an open view of the ankle brace of FIG. 1 removed from the foot and showing the interior thereof.
Figure 4:
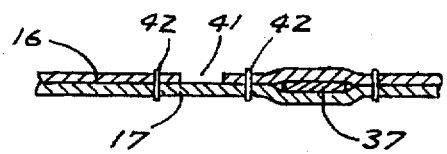
FIG. 4 is an enlarged view of a portion of a section of the ankle brace of FIG. 3 taken along the line 4—4 thereof.

Ankle brace 10 includes a base 15 of flexible sheet-like material. Base 15 is shaped to closely encompass the midfoot portion and ankle of the wearer extending from the leg. As shown in FIG. 2 at the cut-out section thereof, and along the edges of the base, the base 15 includes an outer layer or shell 16 and an inner layer or liner 17 that is substantially co-extensive with the shell 16. The outer layer 16 is of a durable, flexible but inelastic material, such as vinyl. The liner 17 is of a soft material that is flexible as well as elastic, as will more fully be described. Together the outer layer 16 and the liner 17 give strength and durability to the brace 10 and comfort to the foot. The edges of the base can be trimmed with elastic binding.

A reinforcement strip 33, secured by seams 31, extends vertically along the back of base 15.

Base 15 has an upper edge 19 that fits in partial circumferential relationship to the lower leg. Base 15 has lateral and medial forward edges 20, 21 that extend from the upper edge 19 to a front edge 29. Reinforcing stitching 25 extends parallel to the forward edges.

A row of lace eyelets 24 extends parallel to each forward edge. A common lace 28 is trained through the eyelets. A tongue 22 is connected by a fabric hinge 23 to one edge of base 15. A heel opening 34 is located in the rearward portion of base 15 for accommodation of the heel 30 of the foot.

When installed on a foot, base 15 wraps around the foot and ankle. Forward edges 20, 21 come toward one another along the front superior foot and ankle surfaces. The front edge 29 wraps around the bottom of the foot. The tongue 22 covers the front superior foot and ankle. The lace 28 holds the base in place.

Longitudinal pockets 36 are formed by longitudinal seams 35. Pockets 36 can carry resilient stay members 37 comprised of interleaved and flattened helical springs.

A first relief opening 41 is located on the side of the base 15. Relief opening 41 is elongate, slot-shaped opening. It is located in the vicinity of flexure between the ankle and foot. It is arcuate-shaped, so as to be generally parallel to the curvature of the front superior foot surface at the juncture of the ankle and foot. It is located slightly aft of the forward edge 21. Relief opening 41 is comprised of a cut-out portion of the outer layer 16. The opening is spanned by the elastic inner liner 17. Boundary stitching 42 can bound the opening 41 for purposes of durability. Opening 41 is located in that region of the base that is subject to expansion and contraction upon flexure and extension of the foot. Upon flexure in this region, or inward movement of the foot, the material would normally bunch. The liner 17 can be in slight tension across the expanse of the opening provided by the opening 41 whereby upon inward movement of the foot, retraction does not result in bunching. When liner 17 does bunch, it is of a much lesser nature than that of the outer, inelastic shell. Upon extension of the foot, or outward bending, liner 17 stretches to accommodate the movement of the foot. This is in contrast to the inelastic outer shell which would normally inhibit such movement beyond certain limits.

A second relief opening 45 is located in the base 15 in association with the front edge 29 and on the side of the foot. Relief opening 45 is comprised as a V-shaped notch or a triangularly-shaped opening with one edge coextensive with the front edge of the base. The V-shaped notch has sides that are rearwardly convergent. Opening 45 is cut out of the outer layer 16. The opening is spanned by the elastic inner layer 17. Boundary stitching 46 provides durability around relief opening 45.

Upon flexure of the ankle, the opening 45 spreads, permitting a greater degree of freedom of the foot. The liner 17 stretches as the opening spreads. Upon extension of a foot, the opening 45 closes. This lessens or eliminates the bunching of material that would otherwise occur at this area. The perimeter stitching around the openings provides boundaries for the expansion and contraction. The expansion and contraction is accommodated by the elasticity of the inner liner 17. In a preferred embodiment, the inner liner 17 is stretchable only in a horizontal or circumferential direction. Corresponding relief openings 41A, 45A are provided on the opposite side of the base. By way of example, the arcuate relief openings on the sides of the base can be approximately three inches long and one-eighth inch wide.

The first and second relief openings on either side of the base act in concert. When one of the openings closes due to compression that would otherwise cause bunching, the other opens under tension. A greater degree of freedom is afforded to the ankle without compromise of the protection afforded by the ankle brace.

Ankle protection is afforded by a support strap system installed on the inner lateral side of the base, as shown in FIG. 2. A side support strap 49 is fixed to the base by a seam 50 located adjacent the front edge 29 on the lateral side of the base 15. The support strap 49 extends upwardly somewhat parallel to the forward edge 20 to an intermediate location on the base 15 above the apex of the lateral second opening 45A, where it is fixed by an intermediate seam 51. The side support strap 49 is effective to inhibit undue twisting of the foot, particularly anterior movement, upon lateral rotation of the ankle.

An anterior talofibular ligament support strap 54 is fixed at one end to the base near the bottom of the base 15 at the location that is disposed under the foot, secured there by stitching 55. The anterior talofibular ligament support strap 54 extends diagonally upward from that position and is fixed at an opposite end proximate the forward lateral edge 20 at an intermediate position thereon, by stitching 57. The stitching 51 that secures the upper end of the side support strap 49 also secures the anterior talofibular ligament support strap 54 at an intermediate portion thereof with respect to the base 15. The support strap 54 is effective to prevent undue stretching of the anterior talofibular ligament upon twisting of the foot in an outward direction.

While a preferred embodiment of the invention has been shown and described, it will be apparent that deviations from the embodiment shown can be made without departing from the scope and spirit of the invention.

The embodiments of the invention in which an exclusive property or privilege is claimed are defined as follows:

1. An ankle brace comprising:

a base including an outer layer of inelastic, flexible material shaped to encompass the ankle and middle portion of the foot, having lateral and medial forward edges that come toward one another over the front superior foot surface, and having a front edge connected to the forward edges, said front edge extendible around the bottom of the foot; and a plurality of relief openings in said outer layer, each said relief opening comprised as a cut-out section of the outer layer, and an inner layer of elastic material spanning the cut-out section, and means fixing the inner layer of elastic material to a portion of the perimeter of the cut-out section;

one such relief opening located on a first side of the base in the vicinity of the ankle and comprised as a first elongate arcuate slot-shaped opening having a closed boundary and a longitudinal axis that is generally parallel to the curvature of the front superior foot surface and located at the juncture of the ankle and foot; and a second symmetrical elongate arcuate slot-shaped opening having a closed boundary and symmetrically located on the other side of the base.

2. The ankle brace of claim 1 wherein:

said relief openings include a first forwardly-open V-shaped shaped notch at the front edge of the base on one side thereof.

3. The ankle brace of claim 2 including:

a second symmetrical V-shaped notch on the opposite side of the base.

4. The ankle brace of claim 1 including:

a support strap system installed on the inner lateral side of the base.

5. The ankle brace of claim 4 wherein:

said support strap system includes a side support strap fixed at one end to the lateral side of the base adjacent the front edge, extending upwardly generally parallel to the lateral forward edge with the other end fixed at an intermediate location on the base; and an anterior talofibular ligament support strap fixed at one end to the base near the bottom of the foot location, extending diagonally upward with the opposite end fixed proximate the forward lateral edge of the base, and stitching means securing an intermediate section of the strap to the base.

6. An ankle brace comprising:

a base including an outer layer of inelastic, flexible material shaped to encompass the ankle and middle portion of the foot, having lateral and medial forward edges that come toward one another over the front superior portions of the foot, and having a front edge connected to the forward edges, extendible around the bottom of the foot;

a plurality of relief openings in said outer layer, each relief opening comprised as a cut-out section of the outer layer, and an inner layer of elastic material spanning the cut-out section, and means securing portions of the perimeter of the cut-out section to the inner layer;

said relief openings including a first forwardly-open V-shaped notch on a first side of the base with one edge coextensive with the front edge of the base and sides that are rearwardly convergent; and a second forwardly open V-shaped notch on the other side of the base with one edge coextensive with the front edge of the base and sides that are rearwardly convergent.

7. The ankle brace of claim 6 including:

a support strap system installed on the inner lateral side of the base.

8. The ankle brace of claim 7 wherein:

said support strap system includes a side support strap fixed at one end to the lateral side of the base adjacent the front edge, extending upwardly generally parallel to the lateral forward edge with the other end fixed at an intermediate location on the base; and an anterior talofibular ligament support strap fixed at one end to the base near the bottom of the foot location, extending diagonally upward with the opposite end fixed proximate the forward lateral edge of the base, and stitching means securing an intermediate section of the strap to the base.

9. The ankle brace of claim 6 wherein:

said relief openings include first and second elongate arcuate-shaped openings located on either side of the base in the vicinity of the ankle, and each having a longitudinal axis that is generally parallel to the curvature of the front superior foot surface.

10. The ankle brace comprising:

a base including an outer layer of inelastic, flexible material shaped to encompass the ankle and middle portion of the foot, having lateral and medial forward edges that come toward one another over the front superior portions of the foot, and having a front edge connected to the forward edges, extendible around the bottom of the foot;

a support strap system installed on the inner lateral side of the base;

said support strap system including a side support strap fixed at one end to the lateral side of the base adjacent the front edge, extending upwardly generally parallel to the lateral forward edge with the other end fixed at an intermediate location on the lateral side of the base; and an anterior talofibular ligament support strap fixed at one end to the base near the bottom thereof, extending diagonally upward with the opposite end fixed proximate the forward lateral edge of the base, and stitching means securing an intermediate portion of the strap to the base.

* * * * *